(12) United States Patent
Zhang et al.

(10) Patent No.: US 10,537,516 B2
(45) Date of Patent: Jan. 21, 2020

(54) COMPOSITION FOR TREATING SKIN PIGMENTATION AND RELATED METHODS

(71) Applicant: Access Business Group International LLC, Ada, MI (US)

(72) Inventors: Yi Zhang, Shanghai (CN); Qiang Han, Shanghai (CN); Tingzhao Li, Shanghai (CN)

(73) Assignee: ACCESS BUSINESS GROUP INTERNATIONAL LLC, Ada, MI (US)

( * ) Notice: Subject to any disclaimer, the term of this patent is extended or adjusted under 35 U.S.C. 154(b) by 0 days.

(21) Appl. No.: 15/963,275

(22) Filed: Apr. 26, 2018

(65) Prior Publication Data

US 2018/0311142 A1    Nov. 1, 2018

(30) Foreign Application Priority Data

Apr. 28, 2017    (CN) .......................... 2017 1 0292478

(51) Int. Cl.
*A61Q 19/02* (2006.01)
*A61K 8/9783* (2017.01)
(Continued)

(52) U.S. Cl.
CPC ............ *A61K 8/9783* (2017.08); *A61K 8/345* (2013.01); *A61K 8/368* (2013.01); *A61K 8/49* (2013.01);
(Continued)

(58) Field of Classification Search
None
See application file for complete search history.

(56) References Cited

U.S. PATENT DOCUMENTS 4,990,330 A * 2/1991 Oyama ................. A61K 8/347
424/59
5,466,718 A * 11/1995 Nakatsu ............... A61K 31/045
514/557
(Continued)

FOREIGN PATENT DOCUMENTS

CN    1583064 A    2/2005
CN    1827112 A    9/2006
(Continued)

OTHER PUBLICATIONS

PCT International Search Report for PCT/US2018/029507, 2 pages.
(Continued)

*Primary Examiner* — Robert A Wax
*Assistant Examiner* — Melissa S Mercier
(74) *Attorney, Agent, or Firm* — Warner Norcross + Judd LLP (57) ABSTRACT

A composition for treating skin pigmentation, a method of forming the composition, and a method of treating skin pigmentation are disclosed. The composition comprises at least one pharmaceutically acceptable additive. The composition further comprises at least one melanin production inhibitor, which may be a depigmentation agent. The melanin production inhibitor is present in an amount effective to inhibit melanin production in human skin cells of a subject that is administered the composition. The melanin production inhibitor is selected from the group consisting of cyclovirobuxine D, lipoic acid, nuciferine, peimisine, oleuropein, *Rhodiola algida* extract, *Rhodiola kirilowii* (Regel) Maxim extract, *Glycyrrhizae Radix* et *Rhizoma* extract, *Cirsii japonici herba* extract, *Platycladi* semen extract, *Synotis erythropappa* extract, *Astragali complanati* semen extract, *Plantaginis* semen extract, *Lycopi herba* extract, *Euryales* semen extract, *Cuscutae* semen extract, *Amomi fructus* extract, *Tara* seed extract, *Platycladi cacumen*
(Continued)

extract, *Eucommiae cortex* extract, *Dioscoreae rhizoma* extract, *Cirsii herba* extract, and combinations thereof.

20 Claims, 6 Drawing Sheets

(51) Int. Cl.

| | | |
|---|---|---|
| *A61K 8/63* | (2006.01) | |
| *A61K 8/49* | (2006.01) | |
| *A61K 8/368* | (2006.01) | |
| *A61K 8/92* | (2006.01) | |
| *A61K 8/34* | (2006.01) | |
| *A61K 8/9789* | (2017.01) | |
| *A61K 8/9794* | (2017.01) | |
| *A61K 8/06* | (2006.01) | |
| *A61K 8/02* | (2006.01) | |
| *A61K 8/04* | (2006.01) | |

(52) U.S. Cl.
CPC .......... *A61K 8/4926* (2013.01); *A61K 8/4986* (2013.01); *A61K 8/63* (2013.01); *A61K 8/922* (2013.01); *A61K 8/9789* (2017.08); *A61K 8/9794* (2017.08); *A61Q 19/02* (2013.01); *A61K 8/022* (2013.01); *A61K 8/042* (2013.01); *A61K 8/046* (2013.01); *A61K 8/062* (2013.01); *A61K 8/064* (2013.01)

(56) References Cited

U.S. PATENT DOCUMENTS

| | | | |
|---|---|---|---|
| 5,747,006 A | 5/1998 | Dornoff et al. | |
| 5,980,904 A | 11/1999 | Leverett et al. | |
| 6,752,999 B2 * | 6/2004 | Perricone | A61K 8/4986 |
| | | | 424/401 |
| 6,994,874 B2 | 2/2006 | Leverett et al. | |
| 7,060,304 B2 | 6/2006 | Leverett et al. | |
| 7,247,321 B2 | 7/2007 | Leverett et al. | |
| 7,364,759 B2 | 4/2008 | Leverett et al. | |
| 7,897,184 B1 | 3/2011 | Rana et al. | |
| 9,364,423 B2 * | 6/2016 | Suzuki | A61K 8/97 |
| 9,364,424 B2 * | 6/2016 | Caetano | A61K 8/97 |
| 2014/0242013 A1 * | 8/2014 | Yu | A61K 8/97 |
| | | | 424/62 |
| 2017/0252293 A1 | 9/2017 | Brumbaugh et al. | |

FOREIGN PATENT DOCUMENTS

| | | | |
|---|---|---|---|
| CN | 105193898 A | * | 12/2015 |
| CN | 105434217 A | | 3/2016 |
| KR | 20100052092 A | * | 5/2010 |
| KR | 20100052092 A | | 5/2010 |
| WO | WO9920290 A1 | | 4/1999 |

OTHER PUBLICATIONS

Database GNPD [Online] MINTEL; Oct. 31, 2016, Anonymous: "Sun protector SPF 50+PA+++", XP002781861, Database accession No. 4356985 p. 1.

* cited by examiner

COMPOSITION FOR TREATING SKIN PIGMENTATION AND RELATED METHODS

CROSS-REFERENCE TO RELATED APPLICATIONS

This application claims priority to and all advantages of Chinese Patent Application No. 201710292478.X filed on 28 Apr. 2017, the content of which is hereby incorporated by reference.

FIELD OF THE INVENTION

This disclosure provides a composition for treating human skin pigmentation, a method of forming the composition, and a method of treating human skin pigmentation.

BACKGROUND OF THE INVENTION

Melanin is important for protecting human skin from damage induced by radiation. The accumulation of melanin in human skin cells can result in pigmentation disorders, such as melasma, freckles, ephelides, and senile lentigines, also referred to as liver spots or age spots. Aging and exposure to ultraviolet radiation from the sun can increase the occurrence of these and other types of pigmentation disorders.

Melanin is produced in a specialized group of cells known as melanocytes, which are located in the basal layer of the epidermis. Melanin production is controlled at least in part by tyrosinase enzymes and is produced by the oxidation of the amino acid tyrosine, followed by polymerization to produce the pigment melanin.

While melanin is useful in protecting human skin from sun damage, darkening of the skin as a result of melanin production can be aesthetically undesirable to some individuals. Skin lightening treatments and cosmetics are often used by individuals to reduce the appearance of pigmentation disorders, such as freckles or age spots. Conventional cosmetics only temporarily reduce the visibility of the undesirable pigmentation and can be inconvenient to use on a regular basis and on certain parts of the body.

Conventional skin lightening treatments can decrease the appearance of certain pigmentation disorders, but are often associated with undesirable side-effects. Hydroquinone is one example of a common skin lightener, however higher hydroquinone doses may require a prescription from a dermatologist. In some individuals, hydroquinone may cause undesirable discoloration of the skin. Arbutin is an example of a skin lightener that is derived from plants, such as mulberry, cranberry, bearberry and blueberry leaves. Arbutin is a glycosylated hydroquinone and thus may result in undesirable side effects that are similar to hydroquinone in some individuals.

While various efforts have been made, there remains an opportunity to provide additional methods and compositions for treating skin pigmentation disorders, particularly in lightening the appearance of dark spots on the skin and optionally preventing the formation of visible dark spots on the skin.

BRIEF SUMMARY OF THE INVENTION

Disclosed is a composition. The composition can be used for treating human skin pigmentation. The composition comprises at least one pharmaceutically acceptable additive. The composition further comprises at least one melanin production inhibitor. The melanin production inhibitor is selected from the group consisting of cyclovirobuxine D, lipoic acid, nuciferine, peimisine, oleuropein, *Rhodiola algida* extract, *Rhodiola kirilowii* (Regel) Maxim extract, *Glycyrrhizae Radix* et *Rhizoma* extract, *Cirsii japonici* herba extract, *Platycladi* semen extract, *Synotis erythropappa* extract, *Astragali complanati* semen extract, *Plantaginis* semen extract, *Lycopi herba* extract, *Euryales* semen extract, *Cuscutae* semen extract, *Amomi fructus* extract, *Tara* seed extract, *Platycladi cacumen* extract, *Eucommiae cortex* extract, *Dioscoreae rhizoma* extract, *Cirsii herba* extract, and combinations thereof. The melanin production inhibitor is present in an amount effective to inhibit melanin production in human skin cells of a subject that is administered the composition.

A method of forming the composition is also disclosed. The method comprises providing at least one pharmaceutically acceptable additive and providing at least one melanin production inhibitor. The melanin production inhibitor is as described above. The method further comprises combining the pharmaceutically acceptable additive and the melanin production inhibitor to form the composition.

A method of treating human skin pigmentation of a subject is also disclosed. The method comprises providing a topical composition. The method further comprises applying the topical composition to skin of the subject. The topical composition comprises the composition as described above.

The composition and methods are useful for providing a composition for treating pigmentation in a human subject's skin. Treating pigmentation in human skin can include inhibiting melanin production in treated human skin cells. Optionally, treating pigmentation in human skin includes decreasing an amount of melanin present in the subject's skin cells following treatment. The methods and compositions disclosed herein for inhibiting melanin production and optionally decreasing an amount of melanin present in a subject's skin cells can be used to visually lighten the subject's skin and optionally inhibit further darkening of the subject's skin.

According to various embodiments of the invention, a composition for treating pigmentation in human skin includes one or more pharmaceutically acceptable additives and at least one melanin production inhibitor. The at least one melanin production inhibitor can be selected from the group consisting of Cyclovirobuxine D (CAS No. 860-79-7, $C_{26}H_{46}N_2O$, 402.67 g/mol), Lipoic acid (CAS No. 62-46-4, $C_8H_{14}O_2S_2$, 206.32 g/mol), Nuciferine (CAS No. 475-83-2, $C_{19}H_{21}NO_2$, 295.38 g/mol), Peimisine (CAS No. 19773-24-1, $C_{27}H_{41}NO_3$, 427.62 g/mol), Oleuropein (CAS No. 32619-42-4, $C_{25}H_{32}O_{13}$, 540.51 g/mol), *Rhodiola algida* extract, *Rhodiola kirilowii* (Regel) Maxim extract, *Glycyrrhizae Radix* et *Rhizoma* extract, *Cirsii japonici* herba extract, *Platycladi* semen extract, *Synotis erythropappa* extract, *Astragali complanati* semen extract, *Plantaginis* semen extract, *Lycopi herba* extract, *Euryales* semen extract, *Cuscutae* semen extract, *Amomi fructus* extract, *Tara* seed extract, *Platycladi cacumen* extract, *Eucommiae cortex* extract, *Dioscoreae rhizoma* extract, *Cirsii herba* extract, and combinations thereof. The at least one melanin production inhibitor can be present in an amount effective to inhibit melanin production in human skin cells.

In various embodiments, the at least one melanin production inhibitor is present in an amount effective to inhibit tyrosinase enzyme activity in human skin cells. The at least one melanin production inhibitor for inhibiting tyrosinase enzyme activity can be selected from the group consisting of lipoic acid, *Rhodiola algida* extract, *Rhodiola kirilowii*

(Regel) Maxim extract, *Glycyrrhizae Radix* et *Rhizoma* extract, *Cirsii japonici herba* extract, *Platycladi* semen extract, *Synotis erythropappa* extract, and combinations thereof.

In various embodiments, the at least one melanin production inhibitor is present in an amount effective to decrease a concentration of melanin present in human skin cells. The at least one melanin production inhibitor for decreasing a concentration of melanin can be selected from the group consisting of cyclovirobuxine D, lipoic acid, nuciferine, peimisine, *Rhodiola kirilowii* (Regel) Maxim extract, *Platycladi* semen extract, and combinations thereof.

In various embodiments, the pharmaceutically acceptable additives can be selected from the group consisting of water, glycerin, waxes, alcohols, vegetable oils, mineral oils, silicones, fatty esters, fatty alcohols, glycols, polyglycols, and combinations thereof. The composition can be provided in a form including at least one of a gel, a cream, an aerosol spray, a dispersion, an oil-in-water emulsion, a water-in-oil emulsion, a water-in-silicone emulsion, a foam, a liquid, a mousse, a pomade, a powder, a solid, and an ointment suitable for topical application to human skin.

In various embodiments, a blend for inclusion in a topical treatment for human skin includes at least one depigmentation agent. The at least one depigmentation agent can be selected from the group consisting of cyclovirobuxine D, lipoic acid, nuciferine, peimisine, oleuropein, *Rhodiola kirilowii* (Regel) Maxim extract, *Platycladi* semen extract, and combinations thereof. The at least one depigmentation agent can be present in an amount effective to decrease a concentration of melanin present in human skin cells subsequent to application of the topical treatment on human skin.

In various embodiments, a blend for inclusion in a topical treatment for human skin includes at least one melanin production inhibitor. The at least one melanin production inhibitor can be present in an amount effective to inhibit melanin production in human skin cells subsequent to application of the topical treatment on human skin.

In various embodiments, a method of preparing a composition for treating human skin is provided. The method includes providing one or more pharmaceutically acceptable additives and providing at least one melanin production inhibitor in an amount effective to inhibit melanin production in human skin cells.

Without being bound or limited by any particular theory, it is thought that the methods and compositions of this disclosure are useful for treating skin pigmentation, and more particular for lightening of the skin and/or inhibiting darkening of the pigmentation of a subject's skin. These and other objects, advantages, and features of the invention will be more fully understood and appreciated by reference to the detailed description and drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and practiced or carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

Other advantages of the disclosure will be readily appreciated, as the same becomes better understood by reference to the following detailed description when considered in connection with the accompanying drawings wherein.

DETAILED DESCRIPTION OF THE INVENTION

A skin treatment composition, a method for forming a skin treatment composition, and a method of using a composition for skin treatment (e.g. lightening skin of a subject) are disclosed. The skin treatment composition may simply be referred to hereinafter as "the composition." The composition and methods are useful for providing a composition for treating skin pigmentation in a human subject.

As used herein, "treating skin pigmentation" refers to inhibiting melanin production in human skin cells and/or decreasing an amount of melanin present in human skin cells. The term "depigmentation agent" is used to refer to a compound, a plant extract, or a combination of materials that is/are capable of decreasing an amount of melanin present in a skin cell and/or reducing the pigmentation effect of melanin already present in a skin cell. The term "melanin production inhibitor" is used to refer to a compound, a plant extract, or a combination of materials that is/are capable of inhibiting the production of melanin in a skin cell. Treating skin pigmentation can include lightening of a subject's skin, lightening of a dark spot or mole on a subject's skin, inhibiting an increase in pigmentation in the subject's skin (also referred to as "darkening"), and/or inhibiting formation of a dark spot or mole on the subject's skin. Other potential non-limiting benefits are described herein.

The composition includes at least one component capable of inhibiting melanin production in a subject's skin cells. Optionally, the composition includes at least one depigmentation agent for decreasing a concentration of existing melanin in a subject's skin cell(s). In certain embodiments, the composition includes a depigmentation agent different from the melanin production inhibitor. In various embodiments, the composition includes a combination of one or more melanin production inhibitors and one or more depigmentation agents. In certain embodiments, the composition includes a component that is both a melanin production inhibitor and a depigmentation agent.

In various embodiments, the melanin production inhibitor is a compound capable of inhibiting the production of melanin in skin cells. In certain embodiments, the compound for inhibiting the production of melanin in skin cells is selected from the group consisting of cyclovirobuxine D, lipoic acid, nuciferine, peimisine, oleuropein, and combinations thereof. In specific embodiments, the melanin production inhibitor comprises or is cyclovirobuxine D. In other specific embodiments, the melanin production inhibitor comprises or is lipoic acid. In yet other specific embodiments, the melanin production inhibitor comprises or is nuciferine. In further specific embodiments, the melanin production inhibitor comprises or is peimisine. In yet further specific embodiments, the melanin production inhibitor comprises or is oleuropein.

In various embodiments, the melanin production inhibitor is a plant extract capable of inhibiting the production of melanin in skin cells. In certain embodiments, the plant extract for inhibiting the production of melanin in skin cells is selected from the group consisting of an extract (or extracts) of *Rhodiola algida*, *Rhodiola kirilowii* (Regel) Maxim, *Glycyrrhizae Radix* et *Rhizoma* (including *Glycyrrhiza inflata* Bat.), *Cirsii japonici herba* (including *Cirsium japonicum* Fisch. ex DC), *Platycladi* semen (including *Platycladus orientalis* L. Franco), *Synotis erythropappa*, *Astragali complanati* semen (including *Astragalus complanatus* R. Br.), *Plantaginis* semen (including *Plantago asiatica* L. and *Plantago depressa* Willd.), *Lycopi herba* (including *Lycopus lucidus turcz*. Var. *hirtus* Regel), *Euryales* semen (including *Euryale ferox* Salisb.), *Cuscutae* semen (including *Cuscuta australis* R. Br. and *Cuscuta chinensis* Lam.), *Amomi fructus* (including *Amomum villosum* Lour., *Amomum villosum* Lour. var. *xanthioides* T. L. Wu et *Senjen*, and *Amomum longiligulare* T. L. Wu), *Tara* seed (including *Caesalpinia spinose* Kuntze), *Platycladi cacumen* (including *Platycladus orientalis* L. Franco), *Eucommiae cortex* (including *Eucommiae cortex* and *Eucommia ulmoides* Oliv.), *Dioscoreae rhizoma* (including *Dioscorea opposita* Thunb.), *Cirsii herba* (including *Cirsium setosum* (Willd.) MB), and combinations thereof. In further embodiments, the composition includes a combination of compound(s) and/or plant extract(s) capable of inhibiting the production of melanin in skin cells.

In various embodiments, the depigmentation agent is a compound capable of decreasing an amount of existing melanin present in skin cells. In certain embodiments, the depigmentation agent compound is selected from the group consisting of cyclovirobuxine D, lipoic acid, nuciferine, peimisine, oleuropein, and combinations thereof.

In various embodiments, the depigmentation agent is a plant extract capable of decreasing an amount of melanin present in skin cells. In certain embodiments, the depigmentation agent plant extract is selected from the group of an extract (or extracts) of *Rhodiola kirilowii* (Regel) Maxim, *Platycladi* semen, and combinations thereof.

In various embodiments, the composition includes a compound or plant extract that is both a melanin production inhibitor and a depigmentation agent. Examples of components that exhibit both melanin production inhibition capabilities and depigmentation capabilities include cyclovirobuxine D, lipoic acid, nuciferine, peimisine, *Rhodiola kirilowii* (Regel) Maxim extract, and *Platycladi* semen extract. It is to be appreciated that combinations of such components may be used.

In various embodiments, the composition includes at least one melanin production inhibitor and/or depigmentation agent and optionally consists essentially of a melanin production inhibitor and/or depigmentation agent. As used herein, the phrase "consisting essentially of" generally encompasses the specifically recited elements/components for a particular embodiment. Further, the phrase "consisting essentially of" generally encompasses and allows for the presence of additional or optional elements/components that do not materially impact the basic and/or novel characteristics of that particular embodiment. In certain embodiments, "consisting essentially of" allows for the presence of ≤10, ≤5, or ≤1, weight percent (wt. %) of additional or optional components based on the total weight of the skin treatment composition.

In various embodiments, the composition includes one or more pharmaceutically acceptable additives that are inactive ingredients. Examples of inactive ingredients include, but are not limited to, fragrances; preservatives; alcohols, such as ethanol, propyl alcohol and benzyl alcohol; glycerin; binders; flow agents; glyceryl triacetate; vegetable oils, such as hydrogenated vegetable oils; mineral oils; water; silicones, such as silicone oils; silicon dioxide; waxes, such as carnauba wax and beeswax; fatty esters and fatty alcohols; glycols and polyglycols; and combinations thereof. If utilized to form the composition, the inactive ingredient(s) can be used in various amounts and combined with the melanin production inhibitor and/or depigmentation agent to form a composition that is suitable for topical application to human skin. It is to be further appreciated that the amounts of actives described herein can be normalized with respect to 100 parts by weight of the composition to account for the presence of inactive ingredients (if utilized).

As used herein, reference to "plant extract" generally refers to an extract containing material from any species within the identified genus, unless the particular species is identified. Unless otherwise identified, any part of the plant may be used to obtain the extract used in the composition including, but not limited to, the root, stem, rhizome, leaf, flower, fruit, and/or extracts of these parts. The plant extract may be commercially obtained from various resources. In addition, suitable plant extracts can be obtained by using any conventional extraction technique including, but not limited to, one or more techniques described further below.

The melanin production inhibitor can be present in the composition in an amount effective to inhibit melanin production when topically applied to a human skin cell. Optionally, the melanin production inhibitor is present in the composition in an amount effective to inhibit tyrosinase enzyme activity in human skin cells. In various embodiments, the concentration of the melanin production inhibitor is about 20 percent by weight (% wt.) or less. Optionally, multiple melanin production inhibitors are combined or blended for use in a skin treatment composition. When multiple melanin production inhibitors are combined, the individual concentration or combined concentration of each melanin production inhibitor may be an amount effective to inhibit melanin production when topically applied to a human skin cell. Optionally, the individual concentration or combined concentration of each melanin production inhibitor is an amount effective to inhibit tyrosinase enzyme activity in human skin cells.

In various embodiments, the amount of melanin production inhibitor(s) present in the composition can depend upon several factors, including the desired level of melanin inhibition, the melanin inhibiting level in a particular compound, plant extract, or composition, and other factors. In certain embodiments, the melanin production inhibitor(s) is(are) present an amount of from about 0.01 to about 20 part(s) by weight ("pbw") based on 100 pbw of the composition. In further embodiments, the melanin production inhibitor(s) is(are) present in an amount of from about 0.05 to about 15 pbw, optionally about 0.1 to about 10 pbw, or optionally about 1 to about 5 pbw, based on 100 pbw of the composition. Various subranges and amounts between about 0.01 and about 20 pbw, as well as amounts that are less than or greater than these amounts, are also contemplated.

The depigmentation agent can be present in the composition in an amount effective to decrease a concentration of melanin present in a human skin cell. Optionally, the depigmentation agent is present in an amount effective to inhibit melanin production and decrease a concentration of melanin in a human skin cell. In various embodiments, the concentration of the depigmentation agent is about 20 percent by weight (% wt.) or less. Optionally, depigmentation agents are combined or blended for use in a skin treatment composition. When multiple depigmentation agents are combined, the individual concentration or combined concentration of each depigmentation agent may be an amount effective to decrease a concentration of existing melanin present in human skin cells.

In various embodiments, the amount of depigmentation agent(s) present in the composition can depend upon several factors, including the desired level of melanin inhibition, the melanin inhibiting level in a particular compound, plant extract, or composition, and other factors. In certain embodiments, the depigmentation agent(s) is(are) present an amount of from about 0.01 to about 20 pbw based on 100 pbw of the composition. In further embodiments, the melanin production inhibitor(s) is(are) present in an amount of from about 0.05 to about 15 pbw, optionally about 0.1 to about 10 pbw, or optionally about 1 to about 5 pbw, based on 100 pbw of the composition. Various subranges and amounts between about 0.01 and about 20 pbw, as well as amounts that are less than or greater than these amounts, are also contemplated.

The plant extracts can be obtained via conventional extraction methods understood in the art, such as by water (e.g. steam) extraction or by solvent (e.g. alcohol) extraction. The composition of this disclosure is not limited to a particular extraction method, nor is extraction required since suitable extracts (e.g. standardized extracts) are readily available from a number of commercial suppliers. Exemplarily extraction methods are described below.

To obtain an extract, a polar solvent such as an alcohol (e.g. methanol, ethanol, butylene glycol), an ether (e.g. ethyl ether), a ketone (e.g. acetone), an ester (e.g. ethyl acetate), water, or mixtures thereof, can be used as a solvent. Certain extracts can be also obtained by further extracting the extract from the polar solvent with a non-polar solvent. Suitable non-polar solvents include, but are not limited to, ethyl acetate, hexane, dichloromethane, chloroform, or mixtures thereof.

There are a variety of extraction methods that may be used to produce extracts suitable for the composition. These methods include, but are not limited to, the extraction methods disclosed in U.S. Pat. No. 7,897,184, which is hereby incorporated by reference in its entirety and partially reproduced below with respect to some extraction methods. While extraction solvents described specifically mention ethanol, other alcohols such as, but not limited to, isopropyl alcohol, ethyl alcohol, and/or methyl alcohol may be used in addition to or as an alternative to ethanol. Exemplary alcoholic solvents include, but are not limited to, $C_1$-$C_4$ alcohols, such as methanol, ethanol, propanol, isopropanol, and butanol; hydro-alcohols or mixtures of alcohol and water, including hydro-ethanol; polyhydric alcohols, such as propylene glycol and butylene glycol; and fatty alcohols. Any of these alcoholic solvents may be used. Other solvents such as, but not limited to, acetone may also be used as an extraction solvent. Solvent-water blends, e.g. alcohol-water and/or acetone-water blends, of any ratio, may also be used.

In one example, the extracts can be obtained using an organic solvent extraction technique. In another example, solvent sequential fractionation can be used to obtain the extracts. Total hydro-ethanolic extraction techniques can also be used to obtain the extracts. Generally, this is referred to as a lump-sum extraction. Extracts generated in the process will contain a broad variety of phytochemicals present in the extracted material including fat soluble, liposoluble, and water soluble phytochemicals. Following collection of the extract solution, the solvent will be evaporated, resulting in the extract.

Total ethanol extraction may also be used. This technique uses ethanol as the solvent. This extraction technique generates an extract that may include fat soluble, liposoluble, and/or lipophilic compounds in addition to water soluble compounds. Total methanol extraction may also be used in a similar manner with similar results.

Another example of an extraction technique that can be used to obtain the extracts is carbon dioxide supercritical fluid extraction ("SFE"). In this extraction procedure, the material to be extracted is not exposed to any organic solvents. Rather, the extraction solvent is carbon dioxide ($CO_2$), with or without a modifier, in supercritical conditions (e.g. >31.3° C. and >73.8 bar). Those of skill in the art will appreciate that temperature and pressure conditions can be varied to obtain the best yield of extract. This technique generates an extract of fat soluble, liposoluble, and/or lipophilic compounds, similar to total hexane and ethyl acetate extraction techniques, which may also be used.

The composition can be prepared using various methods. For example, actives of the composition, and optionally one or more inactives, can be mixed or blended and compressed or compounded utilizing various techniques understood in the art. The composition of this disclosure is not limited to a particular order of manufacturing steps or method of manufacture.

In various embodiments, the composition is administered topically by application to the subject's skin. The subject is typically a human, and can include men and women of various ages. The method/composition of this disclosure is not limited to a particular subject.

The composition can be in various forms. Examples of suitable forms include solids, gels and liquids. For example, the composition can be formulated for application as a gel, cream, lotion, pomade, mousse, powder, or foam for application to the subject's skin. In another example, the composition can be formulated for spraying onto a subject's skin. The composition can be formulated to be sprayed as either an aerosol spray or pump spray. In still another example, the composition can be formulated for application using a pre-moistened towelette. In another example, the composition can be formulated as a solid that is rubbed onto the subject's skin. In another example, the composition is formulated for delivery through a patch that is adhered to the subject's skin.

Other than the melanin production inhibitors and/or the depigmentation agents (i.e., the "actives" or "active ingredients"), the composition can include pharmaceutically acceptable additives that are inactives (or "inactive ingredients") including, but not limited to, excipients, such as diluents and binders; granulating agents; glidants (or flow aids); fillers; lubricants; preservatives; stabilizers; coatings; disintegrants; fragrances; and pigments. Further examples of inactive ingredients are described above. The active ingredients and the pharmaceutically acceptable additives can be combined or compounded as desired to form an individual dose that provides the desired amount of active ingredient to the human subject when topically applied.

Optionally, the composition may include one or more additional components such as additives. Suitable additives include those understood in the art, including but not limited to, moisturizers, emollients, emulsifiers, surfactants, oils, extracts, skin protectants, disinfectants, antiseptics, drugs and drug substances, analgesic compounds, anti-neuralgic compound, anti-oxidants, blood circulation promoters, anti-depressant compounds, anti-anxiety compounds, anti-stress compounds, sunscreens, insect repellants, preservatives, exfoliants, fragrances, colors, fillers, solvents, vehicles, carriers, other types of additives known to those of skill in the art, and combinations thereof. Such additives may be utilized alone or in combination. In general, the optional additives may be of any type used in personal care products and cosmetic products.

It is to be appreciated that certain components or additives may be classified under different terms of art and just because a component or additive is classified under such a term does not mean that they are limited to that function. If utilized, the additive or additives may be present in the composition in various amounts. Additional ingredients for optional use in the composition are described in U.S. Pat. No. 5,747,006 to Dornoff et al., U.S. Pat. Nos. 5,980,904, 6,994,874, 7,060,304, 7,247,321, and 7,364,759 to Leverett et al., and U.S. Publication No. 2017/0252293 to Brumbaugh et al., the disclosures of which are hereby incorporated by reference in their entirety.

In various embodiments, the method of use may also be referred to as a cosmetic method for skin lightening. Specifically, the composition is useful for and may be used for skin lightening (or whitening). More specifically, the composition can be used for lightening skin of a subject. The subject is typically a human, and can include men and women of various ages. The composition is not limited to a particular subject or location of skin on the subject. For example, a person may apply the composition to their face, neck, arms, hands, chest, torso, legs, feet, etc., or any combination thereof. Such skin areas may be hyper-pigmented or hypo-pigmented.

The composition may be applied as needed, daily, several times per day or in any suitable regimen such that the desired outcome is achieved. In the method of this disclosure, the frequency of administration (e.g. topical application) can depend on several factors, including the desired level of skin lightening or the frequency and/or color of dark spots. Generally, a regimen includes application of the composition once or twice daily to include an administration in the morning and/or an administration in the evening. The amount and/or frequency of application of the composition may depend on several factors, including the level of desired results and the specific composition.

INDUSTRIAL APPLICABILITY

The composition can be used to treat pigmentation in a subject's skin by inhibiting the production of melanin in the subject's skin cells and/or by decreasing a concentration of existing melanin in the subject's skin cells. The composition can be applied to topically to lighten the subject's overall skin appearance and to prevent darkening of the subject's skin as a result of melanin production. Optionally, the composition is applied to a particular area of the subject's skin, such as a dark spot or mole, to lighten the area and/or to prevent further darkening of the area.

Active ingredients suitable for treating pigmentation in a subject's skin include compounds and plant extracts that are capable of inhibiting the production of melanin skin cells and/or are capable of decreasing a concentration of existing melanin in skin cells. Surprisingly, it was discovered that several compounds and plant extracts are capable of inhibiting the production of melanin skin cells and/or are capable of decreasing a concentration of existing melanin in skin cells to the same degree or greater than conventional skin lightening compounds. In addition, many of the compounds and plant extracts of the composition performed similar to or better than conventional skin lightening compounds in in vitro testing, with similar or better toxicity.

The following examples, illustrating the compositions and methods of this disclosure, are intended to illustrate and not to limit the disclosure.

Examples

The effects of the present skin treatment compounds and plant extracts were evaluated in vitro using a B16-F10 (ATCC# CRL-6475) cell model. The B16-F10 cell model is a *Mus musculus* (mouse) melanoma skin cell line. The skin treatment compounds and plant extracts were evaluated for cell toxicity, inhibition of melanin synthesis, inhibition of tyrosinase enzyme activity, and elimination of existing melanin in B16-F10 cells. Tables 1 and 2 below list the 5 skin treatment compounds and 17 skin treatment plant extracts evaluated, respectively.

TABLE 1

| Skin Treatment Compounds | |
| --- | --- |
| Compounds | |
| Cyclovirobuxine D | Peimisine |
| Lipoic acid | Oleuropein |
| Nuciferine | n/a |

TABLE 2

Skin Treatment Plant Extracts
Plant Extracts

| Rhodiola algida | Astragali complanati semen | Tara seed |
| Rhodiola kirilowii (Regel) Maxim | Plantaginis semen | Platycladi cacumen |
| Glycyrrhizae Radix et Rhizoma | Lycopi herba | Eucommiae cortex |
| Cirsii japonici herba | Euryales semen | Dioscoreae rhizoma |
| Platycladi semen | Cuscutae semen | Cirsii herba |
| Synotis erythropappa | Amomi fructus | n/a |

Toxicity

The toxicity of the skin treatment compounds and plant extracts was evaluated using the CellTiter-Glo® (CTG) Luminescent Cell Viability Assay from Promega Corporation. The assay determines the number of viable cells in culture based on quantitation of the ATP present, which is indicative of the presence of metabolically active cells. Hydroquinone is a conventional skin lightening compound and was therefore selected for use as a positive control in the assay.

Cells were treated with either a skin treatment compound or plant extract or the positive control (i.e., hydroquinone) at multiple concentrations within the range of 0.01 to 100 ug/mL for 72 hours. The CellTiter-Glo® reagent was added to the cells and the luminescence was obtained according to the assay instructions provided by Promega Corporation. The $IC_{50}$ was calculated for each skin treatment compound or plant extract and the corresponding positive control. The results are summarized in Table 3 below.

TABLE 3

Cellular Toxicity for the Skin Lightening Compounds & Plant Extracts vs. Hydroquinone

| Skin Treatment Compound/Plant Extract | $IC_{50}$ (Hydroquinone $IC_{50}$) (μg/mL) |
| --- | --- |
| Cyclovirobuxine D | >100 (3.7) |
| Lipoic acid | >100 (2.2) |
| Nuciferine | 62.2 (1.9) |
| Peimisine | >50 (3.4) |
| Oleuropein | 90.3 (3.3) |
| Rhodiola algida extract | >100 (4.4) |
| Rhodiola kirilowii (Regel) Maxim extract | >100 (5.2) |
| Glycyrrhizae Radix et Rhizoma extract | 74.5 (4.1) |
| Cirsii japonici herba extract | 77.6 (7.0) |
| Platycladi semen extract | 78.8 (8.1) |
| Synotis erythropappa extract | >100 (5.9) |
| Astragali complanati semen extract | >100 (5.4) |
| Plantaginis semen extract | >100 (7.0) |
| Lycopi herba extract | >100 (6.8) |
| Euryales semen extract | >100 (3.2) |
| Cuscutae semen extract | 75.9 (4.8) |
| Amomi fructus extract | >100 (4.2) |
| Tara seed extract | >100 (4.2) |
| Platycladi cacumen extract | >100 (9.3) |
| Eucommiae cortex extract | 95.8 (5.0) |
| Dioscoreae rhizoma extract | >100 (4.5) |
| Cirsii herba extract | >100 (4.1) |

Referring to the Figures, FIGS. 1-4 illustrate toxicity curves for Nuciferine, Peimisine, *Platycladi* semen extract, and *Lycopi herba* extract (squares), respectively, compared to a hydroquinone positive control (triangles). The data in Table 3 and FIGS. 1-4 demonstrates that each of the skin lightening compounds and plant extracts are significantly less toxic than the conventional skin lightening compound hydroquinone.

Melanin Synthesis Inhibition

The ability of the skin treatment compounds and plant extracts to inhibit melanin synthesis was evaluated. Melanin is the pigment in skin cells that is responsible for coloring of the skin and various pigmentation disorders, such as age spots and freckles. Inhibition of melanin synthesis may result in lightening of the skin color and/or inhibit further darkening of the skin color. Arbutin is a conventional plant-derived compound used in skin lightening treatments and was therefore selected for use as a positive control.

Procedure

B16-F10 cells were trypsinized using Trypsin-EDTA (GIBCO Cat. #25200-072) and cell density was determined. The cell slurry was diluted to a concentration of 18,000 cells per milliliter (mL) in a growth media containing RPMI 1640 (GIBCO Cat. #22400-089) supplemented with fetal bovine serum (GIBCO Cat. #10099-141). The diluted cell slurry was dispensed into the wells of a 24 well cell culture plate (BD Falcon Cat. #353047) at 1 mL per well (18,000 cells/well). The cells were incubated overnight at 37° C. and 5% $CO_2$ in humid conditions.

The plated cells were treated by preparing a 200× dilution of each skin lightening compound, plant extract, and arbutin (i.e., the positive control; Sigma Cat. #A4256) in 100% dimethyl sulfoxide (DMSO; Sigma Cat. #D2650). 5 μL of the 200× dilution was added to each well. The treated cells were incubated for 72 hours at 37° C. and 5% $CO_2$ in humid conditions. The skin lightening compounds and plant extracts were evaluated at concentrations of 0 (untreated), 10, 50, and 100 μg/mL. Arbutin was evaluated at concentrations of 0 (untreated), 25, 125, and 250 μg/mL.

When the treatment period was completed, the medium from each well was discarded and the cells were washed once with 1 mL per well of DPBS (Dulbecco's Phosphate-Buffered Saline; Biosera Cat. #LM-S2041). The DPBS wash was removed and 150 μL of 1N sodium hydroxide was added to each well for 30 minutes while the cells were incubated at 80° C. to lyse the cells. Next, 145 μL from each well was transferred to an ultraviolet (UV) plate and the remaining 5 μL was tested to determine the protein concentration. The UV absorbance of each well was determined using a plate reader with the primary wave length set to 400 nm.

Melanin synthesis inhibition was determined using the UV absorbance at 400 nm according to the following equation:

% Inh=(Max signal−Compound signal)/(Max signal−Min signal)×100

Where "% Inh" is the percent inhibition of melanin synthesis, the "Max signal" is the UV absorption for untreated cells, and the "Min signal" is the UV absorption of cells treated with 500 μg/mL arbutin.

Results

The results of the melanin synthesis inhibition assay are provided in Table 4 below. The percent of melanin synthesis inhibition for each skin lightening compound and plant extract at the 100 μg/mL treatment concentration is compared with the percent inhibition for arbutin at the 125 μg/mL treatment concentration.

TABLE 4

Melanin Synthesis Inhibition for the Skin Lightening
Compounds & Plant Extracts vs. Arbutin

| Skin Treatment Compound/Plant Extract | % Melanin Synthesis Inhibition Skin Treatment Compound/Plant Extract (Arbutin)* |
|---|---|
| Cyclovirobuxine D | 53.2 (61.4) |
| Lipoic acid | 30.3** (61.4) |
| Nuciferine | 104.3 (65.3) |
| Peimisine | 62.1 (83.8) |
| Oleuropein | — |
| Rhodiola algida extract | 52.5 (97.6) |
| Rhodiola kirilowii (Regel) Maxim extract | 60.8 (97.6) |
| Glycyrrhizae Radix et Rhizoma extract | 30.7 (97.4) |
| Cirsii japonici herba extract | 123.7 (49.8) |
| Platycladi semen extract | 91.4 (83.4) |
| Synotis erythropappa extract | 82.0 (91.4) |
| Astragali complanati semen extract | 80.8 (73.2) |
| Plantaginis semen extract | 75.7 (84.4) |
| Lycopi herba extract | 73.8 (84.4) |
| Euryales semen extract | 63.6 (95.1) |
| Cuscutae semen extract | 62.2 (73.2) |
| Amomi fructus extract | 61.6 (95.1) |
| Tara seed extract | 59.8 (96) |
| Platycladi cacumen extract | 59.1 (93.4) |
| Eucommiae cortex extract | 56.1 (97.4) |
| Dioscoreae rhizoma extract | 46.6 (83.4) |
| Cirsii herba extract | 34.4 (95.1) |

*% inhibition determined for the skin treatment compound/extract at a 100 μg/mL treatment concentration and arbutin at a 125 μg/mL. Values are the average of two treatment wells.
**% inhibition for lipoic acid at a concentration of 50 μg/mL was 53.9%, compared to 61.4% inhibition with treatment of 125 μg/mL arbutin.
—Data not obtained.

FIGS. 5-8 illustrate example melanin synthesis inhibition data for Nuciferine, Peimisine, *Platycladi* semen extract, and *Lycopi herba* extract (squares), respectively, compared to the arbutin positive control (triangles).

The data in Table 4 and FIGS. 5-8 demonstrates that many of the skin lightening compounds and plant extracts tested exhibited similar or increased ability to inhibit melanin synthesis production compared to a higher concentration of the positive control, arbutin.

Tyrosinase Enzyme Activity

The ability of the skin treatment compounds and plant extracts to inhibit tyrosinase enzyme activity was evaluated. Tyrosinase enzyme is involved in melanin production and thus inhibition of tyrosinase may suppress melanin production, which may result in lightening of skin color and/or inhibition of further darkening of skin color. Arbutin is a conventional plant-derived compound used in skin lightening treatments and was therefore selected for use as a positive control.

Procedure

B16-F10 cells were trypsinized using Trypsin-EDTA and cell density was determined. The cell slurry was diluted to a concentration of 18,000 cells per milliliter (mL) in a growth media containing RPMI 1640 supplemented with fetal bovine serum. The diluted cell slurry was dispensed into the wells of a 24 well cell culture plate (BD Falcon Cat. #353047) at 1 mL per well (18,000 cells/well). The cells were incubated overnight at 37° C. and 5% $CO_2$ in humid conditions.

The plated cells were treated by preparing a 200× dilution of each skin lightening compound, plant extract, and arbutin (positive control) in 100% DMSO. 5 μL of the 200× dilution was added to each well. The treated cells were incubated for 72 hours at 37° C. and 5% $CO_2$ in humid conditions. The skin lightening compounds and plant extracts were evaluated at concentrations of 0 (untreated), 10, 50, and 100 μg/mL. Arbutin was evaluated at concentrations of 0 (untreated), 25, 125, and 250 μg/mL.

When the treatment period was completed, the medium from each well was discarded and the cells were washed once with 1 mL per well of DPBS. The DPBS wash was removed and 80 μL of PBS with 0.1% Triton-X was added to each well and the cells were frozen at −80° C. to lyse the cells. The cells were frozen and recovered 3 times. The lysed cells were transferred to a V-bottom plate and centrifuged at 3000 rpm for 10 min. at 4° C. Next, 60 μL of the supernatant for each sample was added to a UV plate and diluted with 140 μL of 3,4-Dihydroxy-L-phenylalanine (L-DOPA; SIGMA Cat. #D9628). The samples were incubated for 1 hour at 37° C. The UV absorbance of each well was determined using a plate reader with the primary wave length set to 475 nm.

Tyrosinase inhibition was determined using the UV absorbance at 475 nm according to the following equation:

$$\% \, Inh = (\text{Max signal} - \text{Compound signal})/(\text{Max signal} - \text{Min signal}) \times 100$$

Where "% Inh" is the percent inhibition of tyrosinase, the "Max signal" is the UV absorption for cells treated with L-DOPA, and the "Min signal" is the UV absorption of cells not treated with L-DOPA.

Results

The results of the tyrosinase enzyme inhibition assay are provided in Table 5 below. The percent of tyrosinase inhibition for each skin lightening compound and plant extract at the 100 μg/mL treatment concentration is compared with the percent inhibition for arbutin at the 125 μg/mL treatment concentration.

TABLE 5

Tyrosinase Inhibition for the Skin Lightening
Compounds & Plant Extracts vs. Arbutin

| Skin Treatment Compound/Plant Extract | % Tyrosinase Inhibition Skin Treatment Compound/Plant Extract (Arbutin)* |
|---|---|
| Lipoic acid | 98.6 (41.8) |
| Rhodiola algida extract | 36.2 (52.8) |
| Rhodiola kirilowii (Regel) Maxim extract | 52.4 (52.8) |
| Glycyrrhizae Radix et Rhizoma extract | 73.3 (13.6) |
| Cirsii japonici herba extract | 63.1 (29.0) |
| Platycladi semen extract | 70.6 (38.3) |
| Synotis erythropappa extract | 56.0 (38.3) |

*% inhibition determined for the skin treatment compound/plant extract at a 100 μg/mL treatment concentration and arbutin at a 125 μg/mL. Values are the average of two treatment wells.

The data in Table 5 demonstrates that many of the skin lightening compounds and plant extracts tested exhibited similar or increased ability to inhibit tyrosinase enzyme activity compared to a higher concentration of the positive control, arbutin.

Melanin Elimination

The ability of the skin treatment compounds and plant extracts to eliminate existing melanin within skin cells was evaluated. Melanin is the pigment in skin cells that is responsible for coloring of the skin and various pigmentation disorders, such as age spots and freckles. Elimination of existing melanin inside a cell may result in lightening of the skin color and/or inhibit further darkening of the skin color.

Arbutin is a conventional plant-derived compound used in skin lightening treatments and was therefore selected for use as a positive control.

Procedure

B16-F10 cells were trypsinized using Trypsin-EDTA and cell density was determined. The cell slurry was diluted to a concentration of 18,000 cells per milliliter (mL) in a growth media containing RPMI 1640 supplemented with fetal bovine serum. The diluted cell slurry was dispensed into the wells of a 24 well cell culture plate at 1 mL per well (18,000 cells/well). The cells were incubated overnight at 37° C. and 5% $CO_2$ in humid conditions.

Following the overnight incubation, the medium was discarded and replaced with 1 mL per well of growth media including 50 μM forskolin (Sigma Cat. #F6886) and 10 μM 8-Methoxypsoralen (8-MOP; Alfa Aesar Cat. #A17108). The cells were then incubated for 72 hours at 37° C. and 5% $CO_2$ in humid conditions.

The plated cells were treated by preparing a 200× dilution of each skin lightening compound, plant extract, and arbutin (positive control) in 100% DMSO. The medium in each well was discarded and replaced with 1 mL/well. 5 μL of the 200× dilution was added to each well. The treated cells were incubated for 72 hours at 37° C. and 5% $CO_2$ in humid conditions. The skin lightening compounds and plant extracts were evaluated at concentrations of 0 (untreated), 10, 50, and 100 μg/mL. Arbutin was evaluated at concentrations of 0 (untreated), 25, 125, and 250 μg/mL.

When the treatment period was completed, the medium from each well was discarded and the cells were washed once with 1 mL per well of DPBS. The DPBS wash was removed and 150 μL of 1N sodium hydroxide was added to each well for 30 minutes while the cells were incubated at 80° C. to lyse the cells. Next, 145 μL from each well was transferred to a UV plate and the remaining 5 μL was tested to determine the protein concentration. The UV absorbance of each well was determined using a plate reader with the primary wave length set to 400 nm.

Melanin elimination was determined using the UV absorbance at 400 nm according to the following equation:

% Inh=(Max signal−Compound signal)/(Max signal−Min signal)×100

Where "% Inh" is the percent of melanin eliminated from the cell, the "Max signal" is the UV absorption for cells treated with forskolin and 8-MOP, and the "Min signal" is the UV absorption of untreated cells.

Results

The results of the melanin elimination assay are provided in Table 6 below. The percent decrease of melanin following treatment with each skin lightening compound and plant extract at the 100 μg/mL treatment concentration is compared with the percent decrease for cells treated with arbutin at the 125 μg/mL treatment concentration.

TABLE 6

Melanin Elimination for the Skin Lightening Compounds & Plant Extracts vs. Arbutin

| Skin Treatment Compound/Plant Extract | % Melanin Elimination Skin Treatment Compound/Plant Extract (Arbutin)* |
|---|---|
| Cyclovirobuxine D | 92.4 (31.2) |
| Lipoic acid | 65.7 (31.2) |
| Nuciferine | 34.1 (37.5) |
| Peimisine | 23.8 (50.4) |
| Oleuropein | 37.0 (50.4) |

TABLE 6-continued

Melanin Elimination for the Skin Lightening Compounds & Plant Extracts vs. Arbutin

| Skin Treatment Compound/Plant Extract | % Melanin Elimination Skin Treatment Compound/Plant Extract (Arbutin)* |
|---|---|
| *Rhodiola kirilowii* (Regel) Maxim extract | 43.1 (70.6)** |
| *Glycyrrhizae Radix* et *Rhizoma* extract | 72.3 (21.2) |

*% inhibition determined for the skin treatment compound/plant extract at a 100 μg/mL treatment concentration and arbutin at a 125 μg/mL. Values are the average of two treatment wells.
**% inhibition determined for the skin treatment compound/plant extract at a 100 μg/mL treatment concentration and hydroquinone at a 100 μg/mL. Values are the average of two treatment wells.

Figure 1:
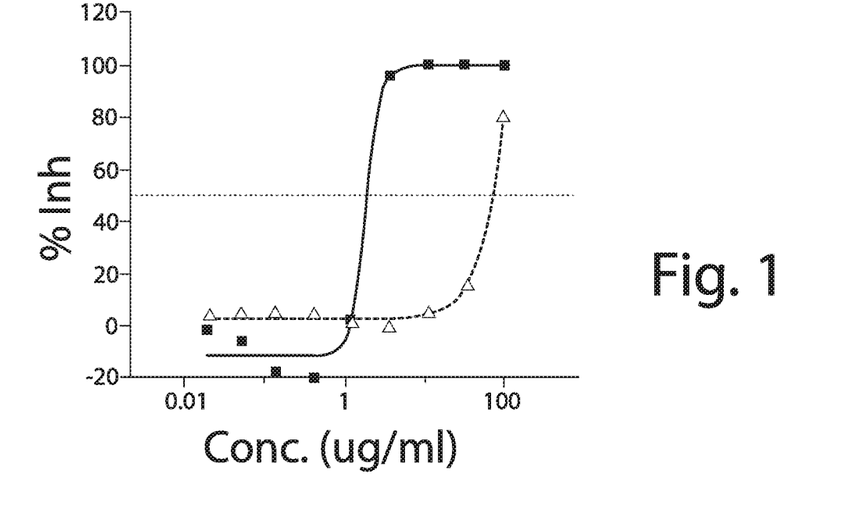
FIG. 1 is a graph illustrating the cell toxicity of nuciferine according to an embodiment.
Figure 2:
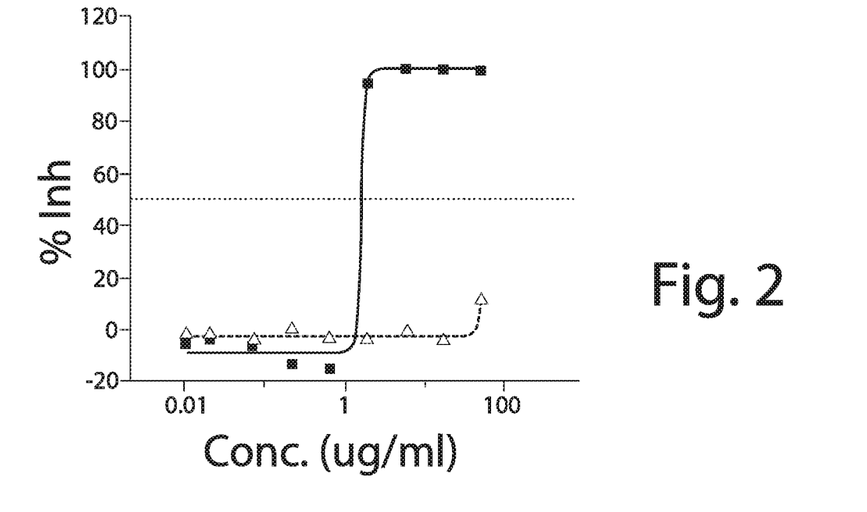
FIG. 2 is a graph illustrating the cell toxicity of peimisine according to an embodiment.
Figure 3:
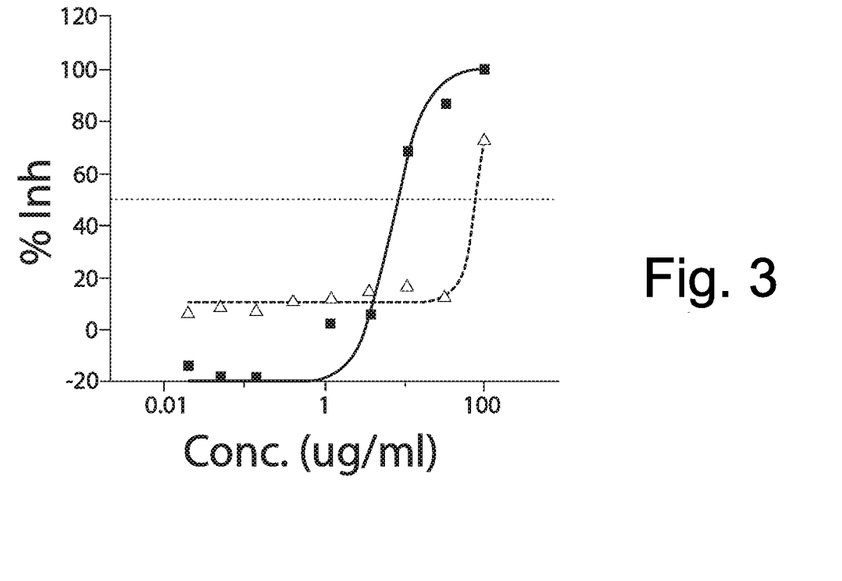
FIG. 3 is a graph illustrating the cell toxicity of *Platycladi* semen extract according to an embodiment.
Figure 4:
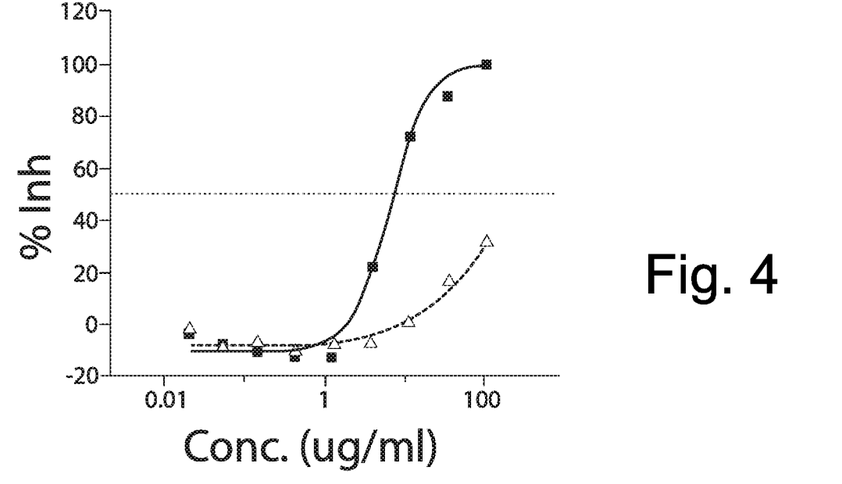
FIG. 4 is a graph illustrating the cell toxicity of *Lycopi herba* extract according to an embodiment.
Figure 5:
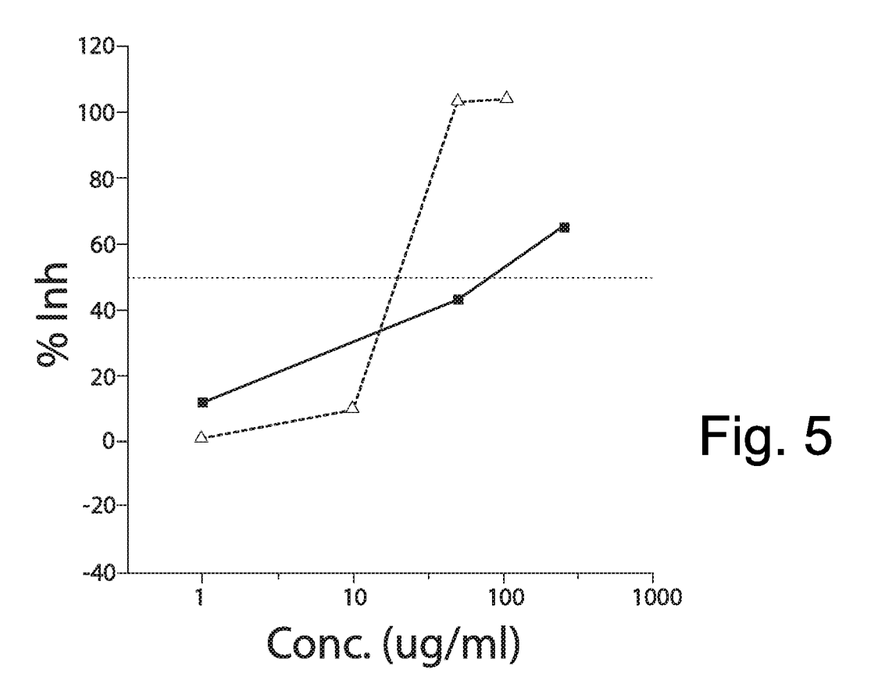
FIG. 5 is a graph illustrating the percent of melanin synthesis inhibition for cells treated with nuciferine according to an embodiment.
Figure 6:
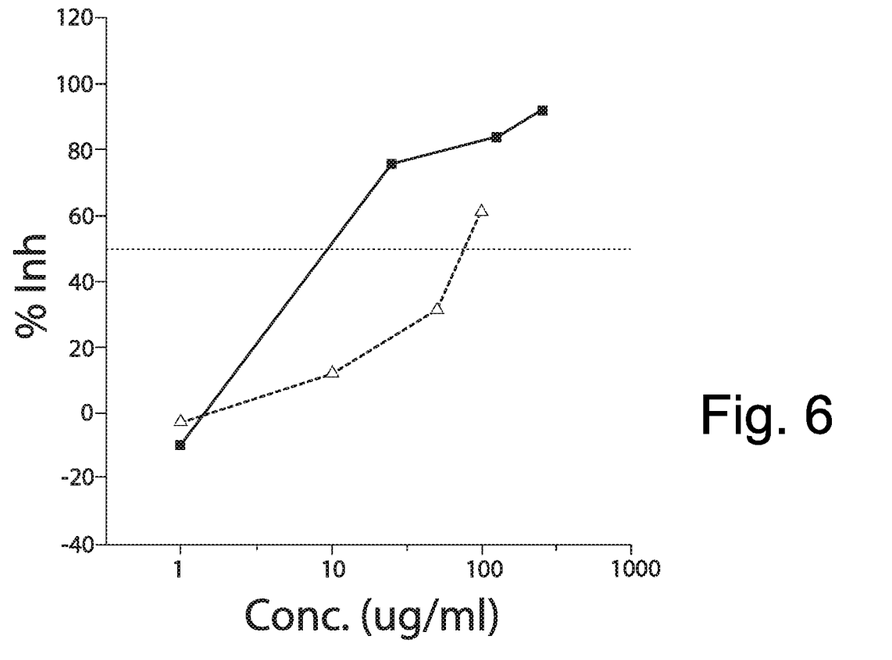
FIG. 6 is a graph illustrating the percent of melanin synthesis inhibition for cells treated with peimisine according to an embodiment.
Figure 7:
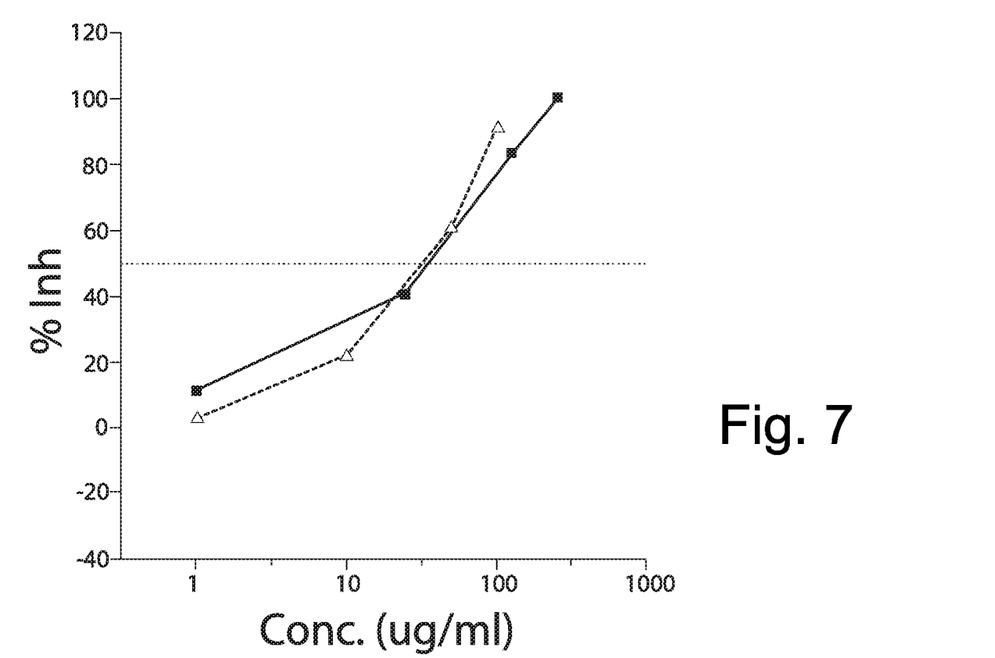
FIG. 7 is a graph illustrating the percent of melanin synthesis inhibition for cells treated with *Platycladi* semen extract according to an embodiment.
Figure 8:
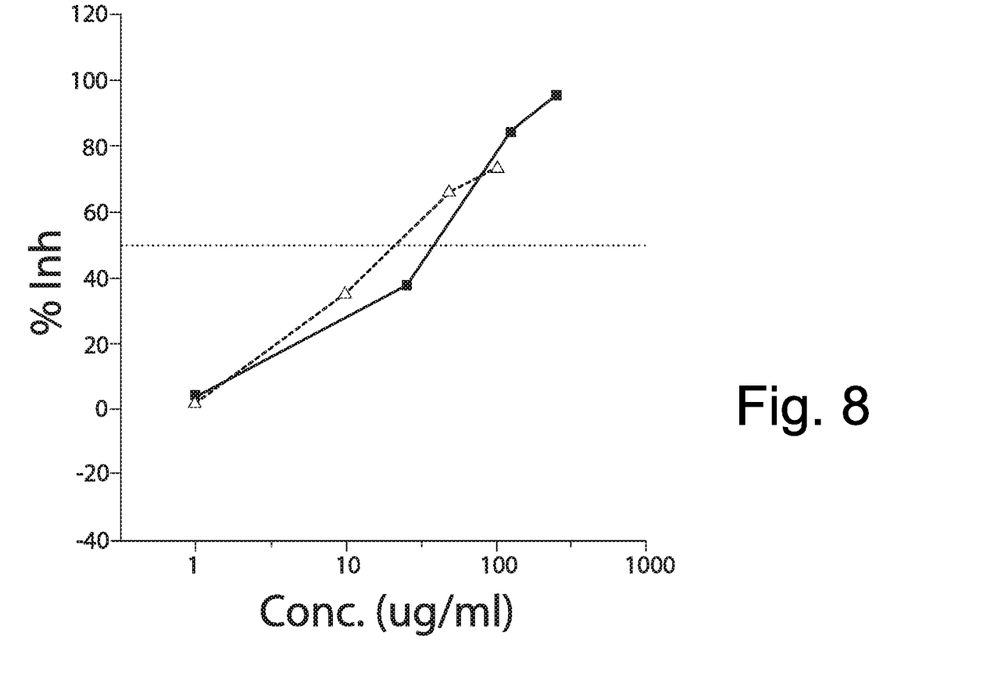
FIG. 8 is a graph illustrating the percent of melanin synthesis inhibition for cells treated with *Lycopi herba* extract according to an embodiment.
Figure 9:
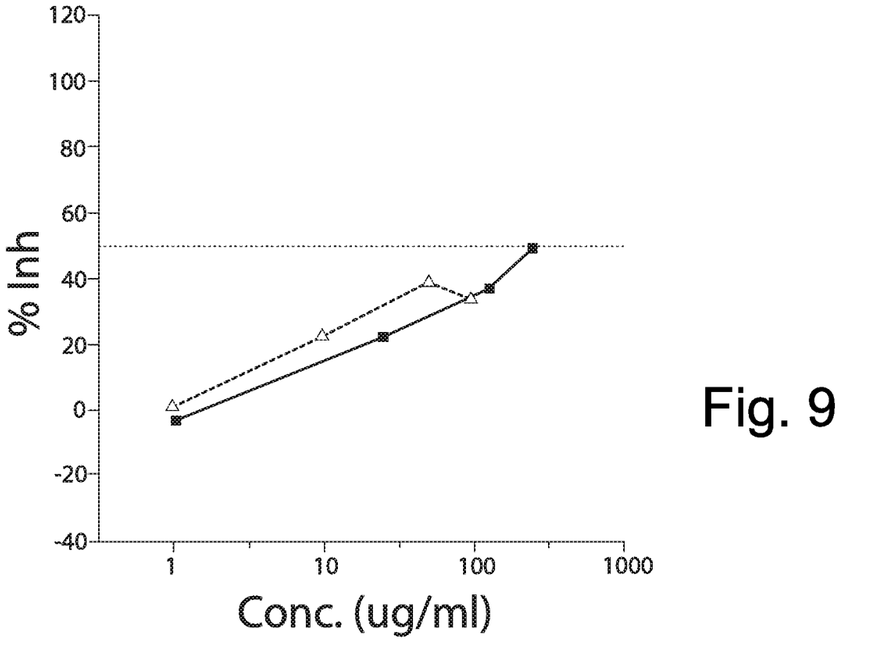
FIG. 9 is a graph illustrating the percent of melanin elimination for cells treated with nuciferine according to an embodiment.
Figure 10:
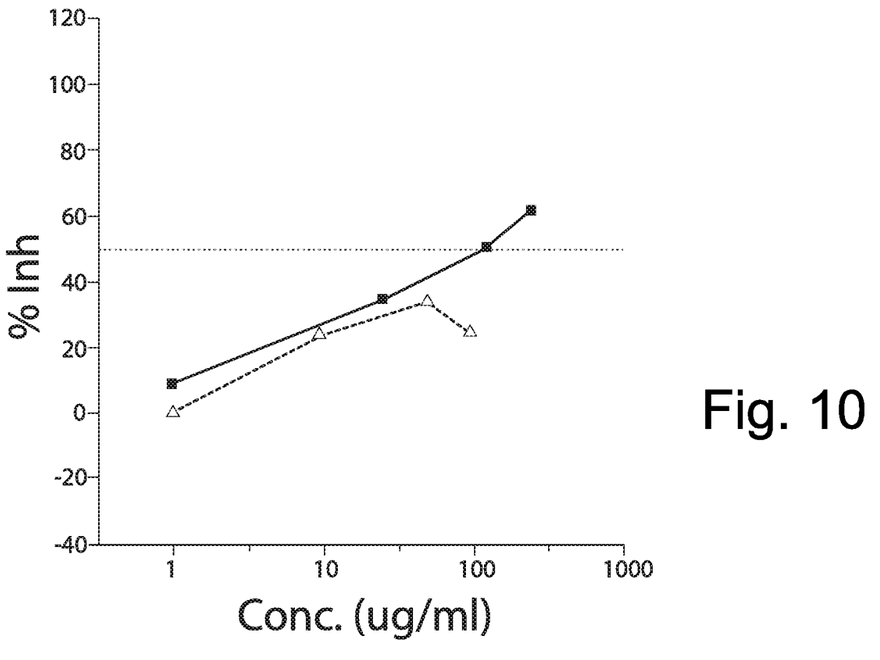
FIG. 10 is a graph illustrating the percent of melanin elimination for cells treated with peimisine according to an embodiment.
Figure 11:
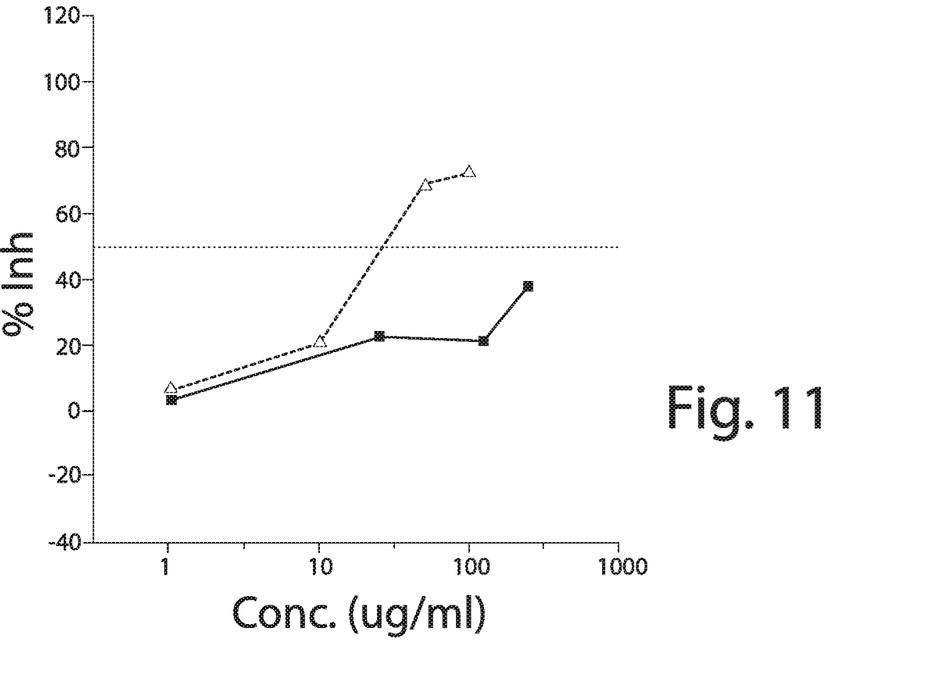
FIG. 11 is a graph illustrating the percent of melanin elimination for cells treated with *Platycladi* semen extract according to an embodiment.

FIGS. 9-11 illustrate example melanin elimination data for Nuciferine, Peimisine, and *Platycladi* semen extract (squares), respectively, compared to the arbutin positive control (triangles). The data in Table 6 and FIGS. 9-11 demonstrates that many of the skin lightening compounds and plant extracts tested exhibited similar or increased ability to eliminate existing melanin within cells compared to a higher concentration of the positive control, arbutin. The ability to eliminate melanin indicates that these compounds and plant extracts may be used in a skin treatment composition as a depigmentation agent to diminish or even eliminate skin spots and undesired skin pigmentation.

The data in Tables 3-5 demonstrates that several of the skin lightening compounds and plant extracts of this disclosure are capable of inhibiting melanin production in cells to a degree similar to a conventional skin lightening compound, and sometimes better than the conventional skin lightening compound, with similar or less toxicity to the cells. Thus, these skin lightening compounds and plant extracts may be used for treating skin pigmentation disorders. The data in Tables 3 and 6 demonstrates that several of the skin lightening compounds and plant extracts of this disclosure are capable of decreasing the concentration of existing melanin in cells to a degree similar to a conventional skin lightening compound, and sometimes better than the conventional compound, with similar or less toxicity to the cells. These skin lightening compounds and plant extracts may be used as depigmentation agents in a skin treatment composition.

An exemplary skin treatment composition can include a combination of nuciferine and peimisine present individually or in combination in an amount effective to inhibit melanin production in human skin cells. The skin treatment composition can include one or more pharmaceutically acceptable additives to form a composition suitable for topical application on a subject's skin. Optionally, nuciferine and peimisine are present individually or in combination in an amount effective to inhibit tyrosinase activity in human skin cells. Optionally, nuciferine and peimisine are present individually or in combination in an amount effective to decrease a concentration of existing melanin present in human skin cells. In various embodiments, nuciferine and peimisine are present in a skin treatment composition in an amount effective to visibly lighten a subject's skin following topical treatment of the subject's skin according to a predetermined treatment schedule. In various embodiments, nuciferine and peimisine are combined to form a blend that can be included in a skin treatment composition for lightening a subject's skin.

Another exemplary skin treatment composition can include a combination of *Platycladi* semen extract and *Lycopi herba* extract present individually or in combination in an amount effective to inhibit melanin production in human skin cells. The skin treatment composition can include one or more pharmaceutically acceptable additives to form a composition suitable for topical application on a subject's skin. Optionally, the *Platycladi* semen extract and *Lycopi herba* extract are present individually or in combination in an amount effective to inhibit tyrosinase activity in human skin cells. Optionally, the *Platycladi* semen extract and *Lycopi herba* extract are present individually or in combination in an amount effective to decrease a concentration of existing melanin present in human skin cells. In various embodiments, the *Platycladi* semen extract and *Lycopi herba* extract are present in a skin treatment composition in an amount effective to visibly lighten a subject's skin following topical treatment of the subject's skin according to a predetermined treatment schedule. In various embodiments, the *Platycladi* semen extract and *Lycopi herba* extract are combined to form a blend that can be included in a skin treatment composition for lightening a subject's skin.

The following additional embodiments are provided, the numbering of which is not to be construed as designating levels of importance.

Embodiment 1 relates to a composition for treating human skin pigmentation, the composition comprising: at least one pharmaceutically acceptable additive; and at least one melanin production inhibitor; wherein the melanin production inhibitor is selected from the group consisting of cyclovirobuxine D, lipoic acid, nuciferine, peimisine, oleuropein, *Rhodiola algida* extract, *Rhodiola kirilowii* (Regel) Maxim extract, *Glycyrrhizae Radix* et *Rhizoma* extract, *Cirsii japonici herba* extract, *Platycladi* semen extract, *Synotis erythropappa* extract, *Astragali complanati* semen extract, *Plantaginis* semen extract, *Lycopi herba* extract, *Euryales* semen extract, *Cuscutae* semen extract, *Amomi fructus* extract, *Tara* seed extract, *Platycladi cacumen* extract, *Eucommiae cortex* extract, *Dioscoreae rhizoma* extract, *Cirsii herba* extract, and combinations thereof; and wherein the melanin production inhibitor is present in an amount effective to inhibit melanin production in human skin cells of a subject that is administered the composition.

Embodiment 2 relates to the composition of Embodiment 1, wherein the melanin production inhibitor is present in an amount effective to inhibit tyrosinase enzyme activity in human skin cells of the subject.

Embodiment 3 relates to the composition of Embodiment 1 or 2, wherein the melanin production inhibitor is selected from the group consisting of lipoic acid, *Rhodiola algida* extract, *Rhodiola kirilowii* (Regel) Maxim extract, *Glycyrrhizae Radix* et *Rhizoma* extract, *Cirsii japonici herba* extract, *Platycladi* semen extract, *Synotis erythropappa* extract, and combinations thereof.

Embodiment 4 relates to the composition of any one of Embodiments 1 to 3, comprising a combination of at least two melanin production inhibitors, optionally at least three melanin production inhibitors.

Embodiment 5 relates to the composition of any one of Embodiments 1 to 4, wherein the melanin production inhibitor is present in an amount of no greater than about 20 percent by weight based on 100 parts by weight of the composition.

Embodiment 6 relates to the composition of Embodiment 1 or 2, wherein the melanin production inhibitor is present in an amount effective to decrease a concentration of melanin present in human skin cells of the subject.

Embodiment 7 relates to the composition of Embodiment 6, wherein the melanin production inhibitor is further defined as a depigmentation agent, and wherein the depigmentation agent is selected from the group consisting of cyclovirobuxine D, lipoic acid, nuciferine, peimisine, *Rhodiola kirilowii* (Regel) Maxim extract, *Platycladi* semen extract, and combinations thereof.

Embodiment 8 relates to the composition of Embodiment 7, comprising a combination of at least two depigmentation agents, optionally at least three depigmentation agents.

Embodiment 9 relates to the composition of Embodiment 7 or 8, wherein the depigmentation agent is present in an amount of no greater than about 20 percent by weight based on 100 parts by weight of the composition.

Embodiment 10 relates to the composition of any one of Embodiments 1 to 9, further comprising a depigmentation agent different from the melanin production inhibitor.

Embodiment 11 relates to the composition of any one of Embodiments 1 to 10, wherein the pharmaceutically acceptable additive is selected from the group consisting of water, glycerin, waxes, alcohols, vegetable oils, mineral oils, silicones, fatty esters, fatty alcohols, glycols, polyglycols, and combinations thereof.

Embodiment 12 relates to the composition of any one of Embodiments 1 to 11, further defined as a topical composition for administration to human skin.

Embodiment 13 relates to the composition of Embodiment 12, wherein the topical composition is in the form of a gel, a cream, an aerosol spray, a dispersion, an oil-in-water emulsion, a water-in-oil emulsion, a water-in-silicone emulsion, a foam, a liquid, a mousse, a pomade, a powder, a solid, or an ointment suitable for topical application to human skin.

Embodiment 14 relates to use of the composition according to any one of Embodiments 1 to 13 for treating human skin pigmentation.

Embodiment 15 relates to a method of forming the composition according to any one of Embodiments 1 to 13, the method comprising: providing at least one pharmaceutically acceptable additive; providing at least one melanin production inhibitor; and combining the pharmaceutically acceptable additive and the melanin production inhibitor to form the composition.

Embodiment 16 relates to a method of treating human skin pigmentation of a subject, the method comprising: providing a topical composition; and applying the topical composition to skin of the subject; wherein the topical composition comprises the composition according to any one of Embodiments 1 to 13.

Embodiment 17 relates to the method of Embodiment 16, further defined as a cosmetic method for skin lightening.

The terms "comprising" or "comprise" are used herein in their broadest sense to mean and encompass the notions of "including," "include," "consist(ing) essentially of," and "consist(ing) of." The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "—" in a range of values is "to" or "through"; a ">" is "above" or "greater-than"; a "≥" is "at least" or "greater-than or equal to"; a "<" is "below" or "less-than"; and a "≤" is "at most" or "less-than or equal to." On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

What is claimed is:

1. A composition for treating human skin pigmentation, the composition comprising:
   at least one pharmaceutically acceptable additive; and
   a melanin production inhibitor comprising at least two melanin production inhibitors;
   wherein the melanin production inhibitors are selected from the group consisting of nuciferine, peimisine, oleuropein, *Rhodiola algida* extract, *Glycyrrhizae Radix* et *Rhizoma* extract, *Cirsii japonici herba* extract, *Platycladi semen* extract, *Synotis erythropappa* extract, *Astragali complanati semen* extract, *Plantaginis semen* extract, *Lycopi herba* extract, *Euryales semen* extract, *Cuscutae semen* extract, *Amomi fructus* extract, *Tara seed* extract, *Platycladi cacumen* extract, *Eucommiae cortex* extract, *Dioscoreae rhizoma* extract, *Cirsii herba* extract, and combinations thereof; and
   wherein the melanin production inhibitor is present in an amount effective to inhibit melanin production in human skin cells of a subject that is administered the composition.

2. The composition of claim 1, wherein the melanin production inhibitor is present in an amount effective to inhibit tyrosinase enzyme activity in human skin cells of the subject.

3. The composition of claim 1, wherein at least one of the melanin production inhibitors is selected from the group consisting of *Rhodiola algida* extract, *Glycyrrhizae Radix* et *Rhizoma* extract, *Cirsii japonici herba* extract, *Platycladi semen* extract, *Synotis erythropappa* extract, and combinations thereof.

4. The composition of claim 1, comprising a combination of at least three melanin production inhibitors.

5. The composition of claim 1, wherein the melanin production inhibitor is present in an amount of no greater than about 20 percent by weight based on 100 parts by weight of the composition.

6. The composition of claim 1, wherein the melanin production inhibitor is present in an amount effective to decrease a concentration of melanin present in human skin cells of the subject.

7. The composition of claim 6, wherein at least one of the melanin production inhibitors is further defined as a depigmentation agent, and wherein the depigmentation agent is selected from the group consisting of nuciferine, peimisine, *Platycladi semen* extract, and combinations thereof.

8. The composition of claim 7, comprising a combination of at least two depigmentation agents, optionally at least three depigmentation agents.

9. The composition of claim 7, wherein the depigmentation agent is present in an amount of no greater than about 20 percent by weight based on 100 parts by weight of the composition.

10. The composition of claim 1, further comprising a depigmentation agent different from the melanin production inhibitor.

11. The composition of claim 1, wherein the pharmaceutically acceptable additive is selected from the group consisting of water, glycerin, waxes, alcohols, vegetable oils, mineral oils, silicones, fatty esters, fatty alcohols, glycols, polyglycols, and combinations thereof.

12. The composition of claim 1, further defined as a topical composition for administration to human skin.

13. The composition of claim 12, wherein the topical composition is in the form of a gel, a cream, an aerosol spray, a dispersion, an oil-in-water emulsion, a water-in-oil emulsion, a water-in-silicone emulsion, a foam, a liquid, a mousse, a pomade, a powder, a solid, or an ointment suitable for topical application to human skin.

14. A method of forming the composition according to claim 1, the method comprising:
providing at least one pharmaceutically acceptable additive;
providing at least one melanin production inhibitor; and
combining the pharmaceutically acceptable additive and the melanin production inhibitor to form the composition.

15. A method of treating human skin pigmentation of a subject, the method comprising:
providing a topical composition; and
applying the topical composition to skin of the subject;
wherein the topical composition comprises the composition according to claim 1.

16. The composition of claim 1, wherein at least one of the melanin production inhibitors is selected from the group of nuciferine, peimisine, *Platycladi* semen extract, *Lycopi herba* extract, and combinations thereof.

17. A composition for treating human skin pigmentation, the composition comprising:
at least one pharmaceutically acceptable additive; and
at least one melanin production inhibitor;
wherein the melanin production inhibitor is present in an amount effective to inhibit melanin production in human skin cells of a subject that is administered the composition;
wherein the melanin production inhibitor is present in an amount effective to decrease a concentration of melanin present in human skin cells of the subject;
wherein the melanin production inhibitor is further defined as a depigmentation agent; and
wherein the depigmentation agent is selected from the group consisting of nuciferine, peimisine, *Platycladi* semen extract, and combinations thereof.

18. The composition of claim 17, comprising a combination of at least two depigmentation agents, optionally at least three depigmentation agents.

19. The composition of claim 17, wherein the depigmentation agent is present in an amount of no greater than about 20 percent by weight based on 100 parts by weight of the composition.

20. A composition for treating human skin pigmentation, the composition comprising:
at least one pharmaceutically acceptable additive; and
at least one melanin production inhibitor;
wherein the melanin production inhibitor is selected from the group of nuciferine, peimisine, *Platycladi* semen extract, *Lycopi herba* extract, and combinations thereof; and
wherein the melanin production inhibitor is present in an amount effective to inhibit melanin production in human skin cells of a subject that is administered the composition.

* * * * *